United States Patent
Galey

Patent Number: 5,910,513
Date of Patent: Jun. 8, 1999

[54] SUBSTITUTED BENZYL DERIVATIVES OF POLYALKYLENE POLYAMINES AND THEIR USE IN COSMETIC AND PHARMACEUTICAL COMPOSITIONS

[75] Inventor: Jean-Baptiste Galey, Aulnay-Sous-Bois, France

[73] Assignee: L'Oreal, Paris, France

[21] Appl. No.: 08/876,585

[22] Filed: Jun. 16, 1997

[30] Foreign Application Priority Data

Jun. 18, 1996 [FR] France ................................ 96 07541

[51] Int. Cl.⁶ .................. A61K 31/135; C07C 211/13
[52] U.S. Cl. ................ 514/649; 514/653; 564/305; 564/336; 564/355; 564/361
[58] Field of Search .................... 564/336, 305, 564/355, 360, 361, 512; 514/653, 649, 663, 673, 674

[56] References Cited

U.S. PATENT DOCUMENTS 5,462,970  10/1995  Bergeron et al. .................. 514/654
5,719,193   2/1998  Bowlin et al. ..................... 514/673

FOREIGN PATENT DOCUMENTS 0277 635   2/1988  European Pat. Off. .
45-37303  11/1970  Japan ............................... 514/674
WO 94 07480  4/1994  WIPO .
WO 94 11338  5/1994  WIPO .

OTHER PUBLICATIONS

Journal of Organometallic Chemistry, vol. 490, Mar. 22, 1995, Lausanne Ch, pp. 143–148, XP000645089 Paul D. Beer et al.; "Towards conformationally dependent redox–responsive molecular switches. New polyferrocene bis benzo crown ether receptors".

Primary Examiner—Shailendra Kumar
Attorney, Agent, or Firm—Nixon & Vanderhye, P.C.

[57] ABSTRACT

A compound being a substituted benzyl derivative of polyalkylene polyamine and corresponding to the following formula:

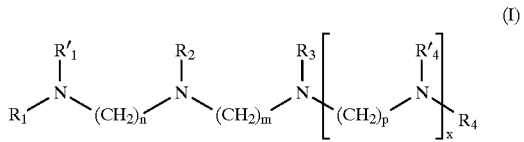

(I)

in which: n and m=2, 3 or 4, p=2 or 3, x=0, 1 or 2, $R_1$ and $R_4$, which may be identical or different, represent
(i) a linear or branched $C_1$–$C_4$ alkyl radical or
(ii) a radical of the following formula:

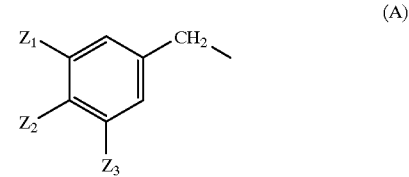

(A)

in which: $Z_1$ represents OH or OR, $Z_2$ and $Z_3$ represent H, OH or OR, R being a linear or branched $C_1$–$C_8$ alkyl radical, $R_2$ and $R_3$, which may be identical or different, represent H, a linear or branched $C_1$–$C_4$ alkyl radical, a radical of formula (A) or a radical of the following formula (B):

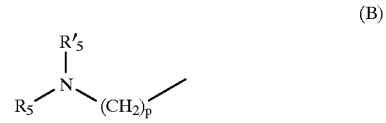

(B)

$R'_1$, $R'_4$ and $R'_5$ represent H or a linear or branched $C_1$–$C_4$ alkyl radical, and $R_5$ represents a linear or branched $C_1$–$C_4$ alkyl radical or a radical of formula (A),
with the proviso that at least one of the radicals $R_1$, $R_2$, $R_3$, $R_4$ or $R_5$ represents a radical of formula (A), and that when $R_1$ and $R_4$, being identical, represent a radical of formula (A), x being 0 or 1, then $Z_1$ or $Z_1$ and $Z_2$, being identical, cannot represent OR, R being a $C_1$–$C_6$ alkyl radical, and their salts and metal complexes.

Use in cosmetic and pharmaceutical compositions in order to protect the body against oxidative stress.

13 Claims, No Drawings

SUBSTITUTED BENZYL DERIVATIVES OF POLYALKYLENE POLYAMINES AND THEIR USE IN COSMETIC AND PHARMACEUTICAL COMPOSITIONS

The present invention relates to novel compounds which are substituted benzyl derivatives of polyalkylene polyamines and which are useful in cosmetic and pharmaceutical compositions to protect the body against oxidative stress.

Oxidative stress is the result of a certain number of physiological and physiopathological situations which lead to a disequilibrium of the antioxidant/pro-oxidant balance.

This disequilibrium is reflected essentially by uncontrolled oxidative processes in living tissues, involving oxygen-containing free radicals and leading to the formation of oxidative damages in biological molecules and macromolecules.

A certain number of physiopathological situations induce, promote, accompany or are the direct consequence of oxidative stress. These are, in particular, inflammation, ageing, exposure to ultraviolet radiation, carcinogenesis, and the toxicity and/or mode of action of certain drugs.

It is known that in the course of oxidative stress, iron is released from its normal storage sites such as ferritin and then becomes available to participate in certain reactions, and in particular in Fenton and Haber-Weiss reactions, thereby allowing the formation of hydroxyl radicals, these radicals being known to be responsible for much of the oxidative damages.

Various compounds which allow the body to be protected against oxidative stress, and in particular synthetic compounds, have been sought for a long time.

These compounds may be grouped into the following main classes:
- antilipoperoxidizing agents such as vitamin E, trolox and butylhydroxytoluene,
- biological reducing agents such as reduced glutathione and its derivatives, and vitamin C and its derivatives,
- singlet-oxygen deactivators (quenchers) such as β-carotene,
- systems capable of decomposing hydrogen peroxide and, in particular, enzymes such as catalase or peroxidases in the presence of their co-substrates,
- systems for protection against the superoxide anion, such as superoxide dismutase (SOD), the Mn-desferal complex or copper diisopropyl salicylate,
- systems capable of decomposing organic hydroperoxides such as glutathione peroxidase or selenium-based model systems,
- iron-chelating agents such as desferal or certain hydroxypyridinones.

However, none of these compounds proved to be really effective with regard to protecting the body against hydroxyl radicals. Although, however, some of them have shown a certain efficacy as hydroxyl-radical traps, they proved to be effective in this respect only at high concentrations, which makes them totally unusable in vivo.

However, certain compounds have been proposed more recently in patent application WO-94/11338 which are capable of forming complexes with iron and whose stability constants are low, consequently decreasing the toxicity risks associated with their use.

From this state of the art, novel compounds have been synthesized and it has been observed that they exert particularly effective protection against attack from hydroxyl radicals generated by the Fenton and Haber-Weiss reactions.

The novel compounds according to the invention, as will be defined below, are of use as active substances for protecting against the harmful effects of free radicals, that is to say against oxidative stress, and in particular for treating pathological conditions in human or veterinary medicine, such as cancers, inflammatory states, reinfusion ischaemia, iron overloads, degenerative diseases of the nervous system, or alternatively for treating the effects of using certain drugs which are known to generate free radicals and, in particular, anti-cancer drugs such as adriamycin.

The compounds according to the invention are also useful in non-pathological conditions, such as exposure to sunlight or ageing, in particular in order to protect the skin or the hair.

The subject of the present invention is thus substituted benzyl derivatives of polyalkylene polyamines corresponding to the following formula:

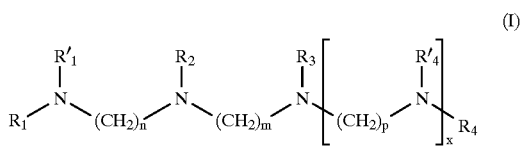

(I)

in which:
n and m=2, 3 or 4,
p=2 or 3,
x=0, 1 or 2,
$R_1$ and $R_4$, which may be identical or different, represent
 (i) a linear or branched $C_1$–$C_4$ alkyl radical or
 (ii) a radical of formula:

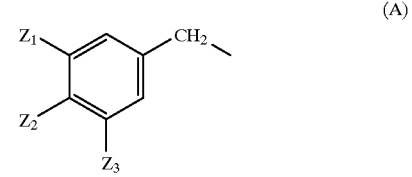

(A)

in which:
$Z_1$ represents OH or OR,
$Z_2$ and $Z_3$ represent H, OH or OR, R being a linear or branched $C_1$–$C_8$ alkyl radical,
$R_2$ and $R_3$, which may be identical or different, represent H, a linear or branched $C_1$–$C_4$ alkyl radical, a radical of formula (A) or a radical of the following formula (B):

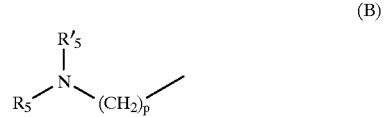

(B)

$R'_1$, $R'_4$ and $R'_5$ represent H or a linear or branched $C_1$–$C_4$ alkyl radical, and
$R_5$ represents a linear or branched $C_1$–$C_4$ alkyl radical or a radical of formula (A),
with the proviso that at least one of the radicals $R_1$, $R_2$, $R_3$, $R_4$ or $R_5$ represents a radical of formula (A), and that when $R_1$ and $R_4$, being identical, represent a radical of formula (A), x being 0 or 1, then $Z_1$ or $Z_1$ and $Z_2$, being identical, cannot represent OR, R being a $C_1$–$C_6$ alkyl radical,
and their salts and metal complexes.

The term linear or branched $C_1$–$C_4$ alkyl radical should be understood to mean radicals such as methyl, ethyl, isopropyl and tert-butyl.

When the linear or branched alkyl radical contains up to 8 carbon atoms, this radical can also be selected from the pentyl, hexyl, isohexyl or octyl radical.

According to a first particularly preferred form of the compounds according to the invention, at least one of the radicals $R_1$, $R_2$, $R_3$, $R_4$ and/or $R_5$ represents a radical of formula (A) in which the radicals $Z_1$, $Z_2$ and $Z_3$, identical or different, represent OH or OR, R being a linear or branched $C_1$–$C_8$ alkyl radical.

Lastly, according to a second more particularly preferred form of the compounds according to the invention, the radicals $Z_1$, $Z_2$ and $Z_3$ are identical and represent a methoxy group, the radical of formula (A) being the 3,4,5-trimethoxybenzyl radical.

Among the salts of the compounds of formula (I), mention may be made in particular of the addition salts of an inorganic acid such as sulphuric acid, hydrochloric acid, nitric acid or phosphoric acid.

Among the complexes, mention may be made of those formed by addition of zinc chloride or calcium chloride.

By way of example, mention may be made of the following compounds, as representative compounds of the compounds of formula (I):

N-(3,4,5-trimethoxybenzyl)-N'{2-[2-(3,4,5-trimethoxybenzylamino)ethylamino]ethyl}ethane-1,2-diamine (tetrahydrochloride), N-(3,4,5-trimethoxybenzyl)-N'(2-{2-[2-(3,4,5-trimethoxybenzylamino)ethylamino]ethylamino}ethyl)ethane-1,2-diamine (pentahydrochloride), N,N'-bis[3-(3,4,5-trimethoxybenzylamino)propyl]butane-1,4-diamine(tetrahydrochloride), N,N'-bis(2-diethylaminoethyl)-N,N'-bis(3,4,5-trimethoxybenzyl)ethane-1,2-diamine, and N-(3,4,5-trimethoxybenzyl)-N',N'-bis[2-(3,4,5-trimethoxybenzylamino)ethyl]ethane-1,2-diamine.

The process for the preparation of the compounds according to the invention is carried out according to conventional synthetic routes which consist in reacting a polyalkylene polyamine with a mono- or polysubstituted benzaldehyde in an organic solvent medium at a temperature below the boiling point of the solvent. The mono- or polybenzylidene amine obtained (Schiff base), which may or may not be isolated, is then reduced in the presence of sodium borohydride or by catalytic hydrogenation. When the compounds according to the invention have a radical of formula (B), the product resulting from the hydrogenation is then reacted with a haloalkyl mono- or dialkylamine under standard conditions for this type of reaction.

Among the starting polyalkylene polyamines, mention may be made in particular of ethylenediamine, diethylenetriamine, tirentine (or triethylenetetraamine), tetraethylenepentamine, spermine (or N,N'-bis(3-aminopropyl)-1,4butanediamine) and tris(2-aminoethyl) amine. Among the substituted benzaldehydes, mention may be made in particular of 3,4,5-trimethoxybenzaldehyde, 3,5-dimethoxybenzaldehyde, 3-hydroxybenzaldehyde, 3,5-dihydroxybenzaldehyde, 3-hydroxy-4-ethoxybenzaldehyde, etc.

Among the haloalkyl mono- or dialkylamines, mention may be made in particular of bromoethyldiethylamine, bromoethyldimethylamine, etc.

The examples given below make it possible to illustrate the methods for obtaining the compounds according to the invention.

The subject of the present invention is also a cosmetic or pharmaceutical composition containing at least one compound of formula (I), or one of its salts or metal complexes, in a cosmetically or pharmaceutically acceptable vehicle.

In these compositions, the active compound of formula (I) is generally present in a proportion of about 0.001 to 10% by weight relative to the total weight of the composition.

The cosmetic compositions may be in various conventional forms such as in the form of an ointment, a cream, a salve, a gel, a spray, a lotion, an emulsion or a vesicle dispersion.

In the compositions according to the invention, it has moreover been observed that the compounds of formula (I) play an important role owing to their antioxidant action and thus the compositions are protected from oxidation.

When the active compound of formula (I) is used in the context of a pharmaceutical treatment, the administration forms may be via the oral, topical or parenteral routes, the pharmaceutically acceptable support being dependent upon the form of administration chosen.

The administration doses are generally between 1 and 1000 mg/kg/day.

The pharmaceutical compositions according to the invention are most particularly intended to treat conditions of oxidative stress associated with certain pathological states and, in particular, neurodegenerative diseases such as, for example, Parkinson's disease, chronic inflammatory conditions, reinfusion ischaemia syndrome, the toxicity of certain drugs such as certain xenobiotics, and iron overloads.

According to a preferred embodiment of the compositions according to the invention, the compound of formula (I) may be combined with at least one other active substance (or one other anti-free-radical substance). These substances may be chosen more particularly from those mentioned above from page 1, line 30 to page 2, line 3

The active compounds of formula (I) and the active substances or the anti-free-radical substances may be combined in the same composition or may be applied separately.

The examples below are given in order to illustrate the preparation of the compounds of formula (I) and their uses in the pharmaceutical and cosmetic fields.

EXAMPLE 1

Preparation of N-(3,4,5-trimethoxybenzyl)-N'-{2-[2-(3,4,5-trimethoxybenzylamino)ethylamino]ethyl}ethane-1,2-diamine tetrahydro-chloride 13.40 g of 3,4,5-trimethoxybenzaldehyde are added to 5 g of triethylenetetraamine dissolved in 200 ml of toluene. After adapting to the reaction vessel a Dean-Stark apparatus, the reaction medium is maintained at reflux for 6 h and is evaporated to dryness.

The residue obtained is taken up in 200 ml of ethanol, to which are added 2.60 g of sodium borohydride at room temperature. After stirring for 24 h and addition of 200 ml of water, the medium is concentrated under vacuum to half its volume. The residual solution is brought to pH 10 by addition of concentrated sodium hydroxide and then extracted with 4×100 ml of dichloromethane. The organic phase is washed with 10% NaCl solution and then dried over sodium sulphate. After evaporation of the solvent, a yellow oil (14.70 g) is obtained, which is taken up in 70 ml of 2N hydrochloric methanol. After stirring for 1 h, the precipitate formed is filtered through a sintered glass and washed with 2×50 ml of ethyl ether. The product is recrystallized from 250 ml of a 9/1 ethanol/water mixture and 6.80 g of N-(3,4,5-trimethoxybenzyl)-N'-{2-[2-(3,4,5-trimethoxybenzylamino)ethylamino]ethyl}ethane-1,2-diamine tetrahydro-chloride are obtained in the form of a white powder.

Melting point=226° C.

NMR spectrum (500 MHz) in DMSO: in accordance with the expected structure.

Elemental analysis: Product in tetrahydrochloride monohydrate form

|         | C     | H    | N    | O     | Cl    |
|---------|-------|------|------|-------|-------|
| Calc. % | 46.57 | 7.16 | 8.35 | 16.71 | 21.19 |
| Found % | 46.59 | 7.19 | 8.15 | 16.97 | 21.03 |

EXAMPLE 2

Preparation of N-(3,4,5-trimethoxy-benzyl)-N'(2-{2-[2-(3,4,5-trimethoxybenzylamino)ethylamino]ethylamino}ethyl)ethane-1,2-diamine pentahydrochloride Starting with 5 g of tetraethylenepentaamine and according to the same operating procedures as those described in Example 1, 3.1 g of N-(3,4,5-trimethoxybenzyl)-N'-(2-{2-[2-(3,4,5-trimethoxybenzylamino)ethylamino]ethylamino}ethyl)ethane-1,2-diamine pentahydrochloride are obtained in the form of a white powder.

Melting point: 220° C. (dec.) (Kofler)

NMR spectrum (500 MHz) in DMSO: in accordance with the expected structure.

Elemental analysis: Product in pentahydrochloride dihydrate form

|         | C     | H    | N    | O     | Cl    |
|---------|-------|------|------|-------|-------|
| Calc. % | 43.78 | 7.29 | 9.12 | 16.68 | 23.12 |
| Found % | 43.97 | 7.32 | 9.03 | 17.09 | 22.80 |

EXAMPLE 3

Preparation of N,N'-bis[3-(3,4,5-trimethoxybenzyl-amino)propyl]butane-1,4-diamine tetrahydrochloride Starting with 5 g of spermine (or N,N'-bis(3-aminopropyl)-1,4-butanediamine) and according to the same operating procedures as those described in Example 1, 10.40 g of N,N'-bis[3-(3,4,5-trimethoxybenzylamino)propyl]butane-1,4-diamine tetrahydrochloride are obtained in the form of a white powder.

Melting point:>250° C. (Kofler)

NMR spectrum (500 MHz) in DMSO: in accordance with the expected structure.

Elemental analysis: Product in tetrahydrochloride + 1.3 H$_2$O form

|         | C     | H    | N    | O     | Cl    |
|---------|-------|------|------|-------|-------|
| Calc. % | 49.22 | 7.74 | 7.66 | 15.97 | 19.41 |
| Found % | 49.56 | 7.92 | 7.68 | 16.21 | 19.11 |

EXAMPLE 4

Preparation of N-(3,4,5-trimethoxybenzyl)-N',N'-bis[2-(3,4,5-trimethoxybenzylaminoethyl]ethane-1,2-diamine trihydrochloride Starting with 5 g of tris(2-aminoethyl)amine and according to the same operating procedures as those described in Example 1, 15 g of N-(3,4,5-trimethoxybenzyl)-N',N'-bis[2-(3,4,5-trimethoxybenzylaminoethyl]ethane-1,2-diamine trihydrochloride are obtained in the form of a white powder.

NMR spectrum (500 MHz) in DMSO: in accordance with the expected structure.

Elemental analysis: Product in trihydrochloride + 1.5 H$_2$O form

|         | C     | H    | N    | O     | Cl    |
|---------|-------|------|------|-------|-------|
| Calc. % | 52.82 | 7.58 | 6.92 | 20.37 | 13.27 |
| Found % | 52.52 | 7.29 | 6.80 | 20.42 | 12.95 |

EXAMPLE 5

Preparation of N,N'-bis(2-diethylaminoethyl)-N,N'-bis(3,4,5-trimethoxybenzyl)ethane-1,2-diamine (a) First step 50 g of 3,4,5-trimethoxybenzaldehyde are suspended in 300 ml of methanol in a 1 liter three-necked flask at room temperature. The mixture is heated to 40° C. in order to obtain complete dissolution and 8.5 ml of ethylenediamine are added dropwise. The reaction medium is then allowed to return to room temperature and, from being clear yellow at the end of the addition of the amine, it rapidly becomes heterogeneous with a precipitation of a yellow solid. The mixture is left stirring for a further hour at room temperature before cooling to 5° C. The precipitate is collected by filtration through a sintered glass, washed thoroughly with cold methanol (3×150 ml) and then resuspended in 250 ml of chilled methanol and filtered in order to remove any trace of residual aldehyde. The white precipitate is then dried under vacuum in a desiccator.

49.4 g of the expected diimine with a melting point=148° C. are obtained.

(b) Second step 20 g of the diimine obtained in the first step are suspended, at room temperature, in 400 ml of absolute ethanol in a 1 liter three-necked flask. 2.27 g of sodium borohydride pellets are then added and the mixture is heated to 55–60° C. The mixture is maintained at 55–60° C. for 2 h and is then allowed to cool slowly to room temperature and is hydrolysed with about 30 ml of aqueous 6N HCl solution to pH<1. The reaction medium turns yellow and a precipitate then appears rapidly. The mixture is then cooled to +5° C. for about 1 h with gentle stirring. The precipitate is then filtered off on a sintered glass and is washed with 50 ml of absolute ethanol before being dried under vacuum in a desiccator.

19.5 g of N,N'-bis(3,4,5-trimethoxybenzyl)ethylenediamine dihydrochloride are obtained in the form of a white powder.

(c) Third step 1.9 g of N,N'-bis(3,4,5-trimethoxybenzyl)ethylenediamine dihydrochloride obtained in the above step are dissolved in 40 ml of acetone. 2.7 g of bromoethyldiethylamine dissolved in 40 ml of acetone are added, followed by 1.40 g of potassium carbonate and the reaction medium is maintained at reflux for 24 h.

After filtering off the salts on paper, the filtrates are evaporated to dryness. The residue is taken up in 30 ml of methanol and 10 ml of 2N hydrochloric methanol. The precipitate formed is filtered off on a sintered glass, washed with 10 ml of methanol and recrystallized from 45 ml of a 4/1 isopropyl ether/methanol mixture. 1.35 g of N,N'-bis(2-diethylaminoethyl)-N,N'-bis(3,4,5-trimethoxybenzyl)ethane-1,2-diamine are obtained in the form of a white powder.

Melting point=218° C.

NMR spectrum (500 MHz) in DMSO: in accordance with the expected structure.

| Elemental analysis: Product in tetrahydrochloride + 0.3 H₂O form | | | | | |
|---|---|---|---|---|---|
| | C | H | N | O | Cl |
| Calc. % | 53.03 | 8.14 | 7.28 | 13.10 | 18.46 |
| Found % | 53.24 | 8.19 | 7.26 | 13.22 | 18.26 |

COSMETIC COMPOSITION EXAMPLES

Example A

An emulsion is prepared, according to the standard techniques, by mixing together the following ingredients:

| | |
|---|---|
| Compound of Example 2 | 0.1% |
| Oxyethylenated PEG 50 | 3% |
| Mono/diglyceryl stearate | 3% |
| Liquid petroleum jelly | 24% |
| Cetyl alcohol | 5% |
| Water qs | 100% |

Example B

An emulsion is prepared, according to the standard techniques, by mixing together the following ingredients:

| | |
|---|---|
| Compound of Example 1 | 0.02% |
| Octyl palmitate | 10% |
| Glyceryl isostearate | 4% |
| Liquid petroleum jelly | 24% |
| Vitamin E | 1% |
| Glycerol | 3% |
| Water qs | 100% |

Example C

The following composition is prepared, according to the standard techniques, by mixing together the following ingredients:

| | |
|---|---|
| Compound of Example 2 | 0.02% |
| Jojoba oil | 13% |
| Alkyl p-hydroxybenzoate (Alkyl parabens) | 0.05% |
| Potassium sorbate | 0.3% |
| Cyclopentadimethylsiloxane | 10% |
| Stearyl alcohol | 1% |
| Stearic acid | 4% |
| Polyethylene glycol stearate | 3% |
| Vitamin E | 1% |
| Glycerol | 3% |
| Water qs | 100% |

PHARMACEUTICAL COMPOSITION EXAMPLES

Example D

| Drinkable suspension | | |
|---|---|---|
| Compound of Example 1 | 0.10 | g |
| Ethanol 90% | 1.00 | g |
| Sorbitol 70% | 0.50 | g |
| Sodium saccharinate | 0.01 | g |
| Methyl p-hydroxybenzoate | 0.04 | g |
| Flavouring qs | 5 | ml |
| Water | | |

Example E

| Tablet | | |
|---|---|---|
| Compound of Example 1 | 0.10 | g |
| Starch | 0.12 | g |
| Dicalcium phosphate | 0.20 | g |
| Lactose | 0.06 | g |
| Magnesium stearate | 0.02 | g |

I claim:

1. A compound which is a substituted benzyl derivative of polyalkylene polyamine and corresponding to the following formula:

$$R_1-N(R'_1)-(CH_2)_n-N(R_2)-(CH_2)_m-\left[N(R_3)-(CH_2)_p\right]_x-N(R'_4)-R_4$$

in which:

n and m=2, 3, or 4, p=2 or 3, x=0, 1 or 2

$R_1$ and $R_4$, which may be identical or different, represent
  (i) a linear or branched $C_1$–$C_4$ alkyl radical or
  (ii) a radical of the following formula:

$$\text{(A)}$$

(aromatic ring with $Z_1$, $Z_2$, $Z_3$ substituents and $CH_2$– group)

in which:

$Z_1$ represents OH or OR, $Z_2$ and $Z_3$ represent H, OH or OR, R being a linear or branched $C_1$–$C_8$ alkyl radical, $R_2$ and $R_3$, which may be identical or different, represent H, a linear or branched $C_1$–$C_4$ alkyl radical, a radical of formula (A) or a radical of the following, formula (B)

$$R_5-N(R'_5)-(CH_2)_p-\quad\text{(B)}$$

$R'_1$, $R'_4$, and $R'_5$ represent H or a linear or branched $C_1$–$C_4$, alkyl radical, and $R_5$ represents a linear or branched $C_1$–$C_4$ alkyl radical or a radical of formula (A), with the proviso that at least one of the radicals $R_1$, $R_2$, $R_3$, $R_4$ or $R_5$ represents a radical of formula (A), wherein $Z_1$, $Z_2$, and $Z_3$ are identical and represent OR, R being a $C_1$–$C_6$ alkyl radical.

2. The compound according to claim 1, wherein the linear or branched $C_1$–$C_4$ alkyl radical is selected from the group consisting of methyl, ethyl, isopropyl and tert-butyl radical.

3. The compound according to claim 1, wherein the linear or branched $C_1$–$C_8$ alkyl radical is selected from the group consisting of methyl, ethyl, isopropyl, tert-butyl, pentyl, hexyl, isohexyl and octyl radical.

4. The compound according to claim 1 wherein the radicals $Z_1$, $Z_2$ and $Z_3$ are identical and represent a methoxy group.

5. The compound according to claim 1 wherein the salts are addition salts of an inorganic acid selected from the group consisting of sulphuric acid, hydrochloric acid, nitric acid and phosphoric acid.

6. The compound according to claim 1 wherein the metal complexes are formed by addition of zinc chloride or of calcium chloride.

7. The compound according to claim 1 which is selected from the group consisting of:
N-(3,4,5-trimethoxybenzyl)-N-{2-[2-(3,4,5-trimethoxybenzylamino)ethylamino]ethyl}ethane-1,2-diamine (tetrahydrochloride), N-(3,4,5-trimethoxybenzyl)-N'(2-{2-[2-(3,4,5-trimethoxybenzylamino)ethylamino]ethylamino}ethyl)ethane-1,2-diamine (pentahydrochloride),
N,N'-bis[3-(3,4,5-trimethoxybenzylamino)propyl]butane-1,4-diamine(tetrahydrochloride),
N,N'-bis(2-diethylaminoethyl)-N,N'-bis(3,4,5-trimethoxybenzyl)ethane-1,2-diamine, and
N-(3,4,5-trimethoxybenzyl)-N',N'-bis[2-(3,4,5-trimethoxybenzylamino)ethyl]ethane-1,2-diamine.

8. A cosmetic or pharmaceutical composition containing, in a cosmetically or pharmaceutically acceptable vehicle, at least one compound of formula (I) as claimed in claim 1.

9. The composition according to claim 8, wherein the compound of formula (I) is present in a proportion of about 0.001 to 10% by weight relative to the total weight of the composition.

10. The composition according to claim 8 which further contains at least one active substance selected from the group consisting of antilipoperoxidizing agents, biological reducing agents, singlet-oxygen deactivators, enzymes, a superoxide dismutase (SOD), the Mn-desferal complex, copper diisopropyl salicylate, glutathione peroxidase and selenium-based systems.

11. A process for the treatment of oxidative stress conditions associated with certain pathological states comprising administering to a human subject in need an effective amount of a pharmaceutical composition according to claim 8.

12. A process for protecting the skin and the hair from sunlight and aging comprising administering to a human subject in need of such protection, an effective amount of a cosmetic and/or pharmaceutical composition according to claim 8.

13. A cosmetic or pharmaceutical composition containing as an antioxidant an effective amount of a compound according to claim 1 thus enabling the said composition to be protected from oxidation.

* * * * *